United States Patent
Wu et al.

(10) Patent No.: US 6,565,872 B2
(45) Date of Patent: *May 20, 2003

(54) POLYMERIC SYSTEM FOR DRUG DELIVERY AND SOLUTE SEPARATION

(75) Inventors: Xiao Yu Wu, 125 Armadale Ave., Toronto, Ontario (CA), M6S 3X3; Frank Yam, North York (CA)

(73) Assignee: Xiao Yu Wu, Toronto (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/504,884

(22) Filed: Feb. 16, 2000

(65) Prior Publication Data

US 2002/0001571 A1 Jan. 3, 2002

Related U.S. Application Data

(60) Provisional application No. 60/120,064, filed on Feb. 16, 1999.

(51) Int. Cl.[7] ............................. A61F 2/00; A61K 9/14; A61K 31/74
(52) U.S. Cl. ...................... 424/426; 424/488; 424/428; 424/486; 424/484; 424/489; 424/78.04
(58) Field of Search ................................. 424/484, 426, 424/486, 488, 489, 427, 428, 464; 514/912, 913, 914, 915

(56) References Cited

U.S. PATENT DOCUMENTS

| 5,226,902 A | | 7/1993 | Bae et al. |
|---|---|---|---|
| 5,599,534 A | * | 2/1997 | Himmelstein et al. ... 424/78.04 |
| 5,840,338 A | * | 11/1998 | Roos et al. .................. 424/488 |

OTHER PUBLICATIONS

Chun SW, Kim JD. A novel hydrogel–dispersed composite membrane of poly(N–isopropylacrylamide) in a gelatin matrix and its thermally actuated permeation of 4–acetamidophen. *Journal of Controlled Release* 38 (1996) 39–47.

Chung, DJ, Ito Y, Imanishi Y. An insulin–releasing membrane system on the basis of oxidation reaction of glucose. *J. Controlled Release* 18 (1992) 45–54.

(List continued on next page.)

*Primary Examiner*—James M. Spear
*Assistant Examiner*—Blessing Fubara
(74) *Attorney, Agent, or Firm*—Bereskin & Parr (57) ABSTRACT

Described is a composite polymeric system to provide enhanced stimuli-responsiveness. The first aspect provides particles where the particles are made of stimuli-responsive polymer which responds to various stimuli such as temperature and pH change. Incorporated with this particle is a second polymer which in turn is relatively insensitive to stimuli. The invention can be potentially applied to other systems comprising a swellable hydrogel and a nonswellable hydrophobic polymer.

23 Claims, 10 Drawing Sheets

OTHER PUBLICATIONS

Iwata H, Oodate M, Uyama Y et al. Preparation of temperature-sensitive membranes by graft polymerization onto a porous membrane. *Journal of Membrane Science* 55 (1991) 119–130.

Okano T, Bae YH, Jacobs, H. and Kim SW. Thermally on–off switching polymers for drug permeation and release. *J. Controlled Release* 11(1990) 255–65.

Lee YM, Shim JK. Preparation of pH/temperature responsive polymer membrane by plasma polymerization and its riboflavin permeation. *Polymer* 38 (1007) 1227–32.

Lin YY, Chen KS, Lin SY. Development and investigation of a thermo–responsive cholesteryl oleyl carbonate–embedded membrane. *Journal of Controlled Release* 41 (1996) 163–170.

Martin GR, Jain RK. Noninvasive measurement of interstitial pH profiles in normal and neoplastic tissue using fluorescence ratio imaging microscopy. *Cancer Research* 54 (1994) 5670–74.

Yoshida R, Kaneko, Y, Sakai, K., Okano T. et al. Positive thermosensitive pulsatile drug release using negative thermosensitive hydrogels. *Journal of Controlled Release*. 32 (1994) 97–102.

Park YS, Ito Y, Imanishi Y. Permeation control through porous membranes immobilized with thermosensitive polymer. *Langmuir* 14 (1998) 910–914.

Spohr R, Reber N, Wolf A et al. Thermal control of drug release by a responsive ion track membrane observed by radio tracer flow dialysis. *Journal of Controlled Release* 50 (1998) 1–11.

Wu XY, Lee PI. Preparation and characterization of thermal and pH sensitive nanospheres. *Pharm. Res.* 10 (1993) 1544–47.

Wu X, Pelton RH, Hamielec AE et al. The kinetics of poly(N–isopropylacrylamide) microgel latex formation. *Colloid Polym Sci.* 272 (1994) 467–77.

Yam F. Wu XY, Zhang Q, A novel composite membrane for temperature and pH responsive permeation, in: *Controlled Drug Delivery: Designing Technology for the Future*, Ed K. Park, ACS, Washington, DC, 2000 pp. 263–272.

Wu XY, Yam F, A novel composite membrane for temperature responsive permeation, *Polymer Preprint* 40 (1999) 312–313.

Ichikawa H, Fukumori Y, A novel positively thermosensitive controlled release microcapsule with membrane of nano-sized poly (N–isopropylacrylamie) gel ispesed in ethylcellulose matrix, *J. Controlled Release*, 63 (2000) 107–119.

* cited by examiner

POLYMERIC SYSTEM FOR DRUG DELIVERY AND SOLUTE SEPARATION

This application claims benefit of provisional application 60/120,064 filed Feb. 16, 1999.

FIELD OF THE INVENTION

The present invention relates to a polymeric system, and more particularly to a system which releases drugs in response to environmental stimuli or separates solutes.

BACKGROUND OF THE INVENTION

The human body has its own homeostatic mechanisms to regulate a variety of physiologic parameters within a certain range. These parameters include temperature, pH and salt content. In instances of disease, however, these parameters may be affected due to various mechanisms. It is essential that the body maintain homeostasis for proper conditions for enzyme reactions and metabolism to be carried.

In infection, the interactions between polymorphonuclear cells and bacteria may result in the production of pyrogens. These pyrogens may disrupt the thermo-regulatory system located in the hypothalamus of the mid-ventricle in the brain resulting in an elevation of the temperature threshold and the normal body temperature. (1) Also, in localized inflammation, the immune system of the body responds with an increase in vasodilation and release of many inflammatory mediators. Histamine, for example, results in an increase in vasodilation and consequently, the permeability of capillaries increases (2) with resulting edema. Sites of inflammation also manifest with an increase in temperature. Products of reactions resulting from inflammation are usually acidic. Therefore, the pH of the local area is reduced.(3)

In tumors, research has demonstrated that the intracellular region is of a lower pH than the extracellular region.(4) Hyperthermia has also been studied as an adjunct in cancer chemotherapy. It was found that tumor cells were more sensitized to chemotherapeutic agents when heat was applied locally to the tumor site.(5)

Regulated drug delivery, or more appropriately called, stimuli-responsive drug delivery, is a concept in which a drug or drugs is/are delivered at an appropriate rate in response to stimuli. As aforementioned, disease states may cause a change in some parameters of the body and this can be used as a stimuli or a "trigger" for the onset and offset of the delivery of drugs. Certain polymers exhibit property changes in response to variations in temperature, and pH. A number of these polymers have been investigated extensively and some success in drug delivery with them has been achieved. For example, polymers loaded with glucose oxidase have been used for regulated delivery of insulin according to the amount of glucose in the body. The glucose reacts with glucose oxidase producing an acid which induce the swelling of the polymer thus increasing the release of insulin.(6) Thermosensitive polymers such as poly(N-isopropylacrylamide) (PNIPAm) have also been used for regulated drug delivery. Such polymers experience a dramatic change in hydration when the temperature is increased or decreased through the phase transition temperature ($T_{tr}$). At $T<T_{tr}$, the polymers swell and release more drug; at $T>T_{tr}$, the polymers collapse resulting in a decrease in release rate due to the formation of dense skin following a pulsatile release at the initial stage.(7) However, in light of this, type of delivery system suffers from negative thermosensitivity, i.e., which is in the opposite direction of the slow of therapeutic agents associated with hyperthermia. In addition the system has the disadvantages of slow response and low mechanical strength.

To overcome these problems, several new designs of thermosensitive delivery systems have been developed. (8–13) These include a hydrogel-valve cylindrical device (14) and various membrane systems. Positive thermoresponse (i.e., higher release rate at higher temperature) has been obtained and mechanical strength has been improved in these systems. However, their application is limited by the methods of fabrication. For example, one is a cylindrical device with a hard plastic shell in which a drug solution is enclosed. The release of the drug solution is controlled by a piece of hydrogel which changes volume with temperature. Unfortunately, the volume change of the hydrogel is rather slow because of its size. Moreover, the device, with a rigid shape, requires surgery for introduction and removal from the body.

Existing membrane systems that exhibit positive thermosensitivity are prepared by chemical reactions such as cross-linking, grafting or radical polymerization.(8–13) Therefore, purification is required after the fabrication of the membrane. More importantly, and a clear disadvantage of such systems is that the reaction conditions are hazardous for therapeutic agents, especially those biological products such as proteins and peptides.

The human body is known to exhibit certain circadian rhythms according to different times of day. It has been found that for some anti-cancer agents, their toxicity can be minimized if the drug is administered at a certain time of the biological clock. Tumor cells are found to multiply at different rates during different time of the day. They are also known to follow a circadian rhythm. Clinical trials have demonstrated that therapeutic agents administered according to circadian rhythms are more effective and less toxic than the standard schedule of therapy.(15) Therefore, pulsatile delivery of drugs may be advantageous over the constant delivery.

With the development of recombinant DNA technology in the production of proteins and peptides, more and more new protein and peptide drugs are synthesized. In biotechnological processes such as fermentation, a number of peptides may be produced in one batch. These processes require further purification of the products.(16) Therefore, it is necessary to design a membrane that can separate a series of compounds of various molecular weights.

In vivo instability especially enzymatic degradation, hinders application of proteins and polypeptides as therapeutic agents. As such it is desirable to have a delivery system that can allow therapeutic agents to diffuse out while preventing the enzymes from entering.

SUMMARY OF THE INVENTION

This invention involves the development of a composite polymeric system containing stimuli-responsive particles and at least one other polymer. As used herein, the term "particles" includes nano- or microspheres, or any other particles having dimensions within the range from nanometeres to millimeteres. The system and particles can be of any shape. This new system can be made to be biocompatable and can be biodegradable. The system can change pore size quickly in response to external stimuli such as pH, temperature, ionic strength, multivalent ions, and other chemicals, i.e., it is stimuli-responsive and consequently it can provide stimuli-responsive drug release. Further, pore size of the system can be tailored for release and/or separation of solutes of different sizes. It can also protect protein and polypeptide drugs from enzymatic degradation.

Broadly stated, the present invention relates to a composite polymer system comprising stimuli-responsive particles, preferably nano- or microspheres, and at least one other polymer. The "at least one other polymer" is referred to herein as a second polymer. Second polymer can be one or more other polymers, i.e., one, two three or more "second polymers". The invention provides a polymeric system which strengthens the mechanical strength of a responsive component using at least one other polymer, i.e., second polymer which acts as a matrix and to increase the response rate of the system. A responsive component such as PNIPAm/MAA nanoparticles act as responsive nanovalves which can form channels in response to changes in external stimuli like temperature and pH. This invention can potentially be applied to other systems comprising a swellable hydrogel and nonswellable hydrophobic polymer.

Accordingly, the present invention provides a composition for a composite polymer system comprising a stimuli-responsive polymer, preferably swellable, and at least one second polymer, preferably non-swellable and hydrophobic.

According to a preferred embodiment the stimuli-responsive polymer is selected from the group consisting of R-acrylamide, $R_1$-acrylate, $R_2$-acrylic acid, and polyethylene glycol where R, $R_1$, and $R_2$ may each be H or alkyl.

According to another preferred embodiment the second polymer is selected from the group consisting of polysaccharides, polysaccharide derivatives, cellulose, cellulose derivatives, polyesters; anhydrides; poly(orthoesters); and polyurethane. Most preferably a composition according to this invention is biocompatable and biodegradable. A preferred embodiment is a composite polymer system comprising poly(N-isopropylacrylamide-co-methacrylic acid) and ethylcellulose.

The invention also broadly contemplates methods for preparing composite polymeric systems of the present invention containing stimuli-responsive particles, preferrably nano- or microspheres, and at least one second polymer as follows:

(a) obtaining particles with suitable responsive properties and sizes;

(b) mixing the particles with at least one second polymer solution;

(c) casting the composite polymer system. The system can be case in any shape which is desired or appropriate depending upon the application.

Accordingly, the present invention provides a method of preparing composite polymer system, preferably with particles that are nano or microspheres comprising: (a) preparing particles with a stimuli-responsive polymer; (b) adding and mixing at least one second polymer, preferably non-swellable and hydrophobic, under conditions which permit dispersion of the particles in the second polymer; and (c) casting the resulting composite polymer system.

According to a preferred method the stimuli-responsive polymer is selected from the group consisting of R-acrylamide, $R_1$-acrylate, $R_2$-acrylic acid, and polyethylene glycol where R, $R_1$, and $R_2$ may each be H or alkyl.

According to a further preferred method the second polymer is selected from the group consisting of polysaccharides, polysaccharide derivatives, cellulose, cellulose derivatives, polyesters; anhydrides; poly(orthoesters); and polyurethane.

According to preferred embodiments the step of mixing is carried out by melting the polymers or mixing them in solution.

The composite polymeric systems of the present invention may also be used in any one or more of the following applications: solute separation and filtration; temperature, pH and ionic strength and biochemical ions—responsive drug delivery; diagnostic and monitoring tools; protein and peptide drug delivery; and coating and microencapsulation of solid dosage forms such as tablets, or microencapsulation of live cells.

According to further embodiments of the present invention the particles may also be used for treating inflammation, infection, diabetes, arthritis, and cancer, as well as a method for stimuli-responsive separation of solutes of different sizes in an aqueous medium.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Composition of the Polymeric System

The polymeric system contains stimuli-responsive nano- and/or microparticles comprising at least one compound including R-acrylamide, $R_1$-acrylate, $R_2$-acrylic acid, where R=H, alkyl, $R_1$=H, alkyl, $R_2$=H, alkyl, and at least one polymer including cellulose and derivatives, e.g., cellulose, ethylcellulose, methylcellulose, propylcellulose, methoxypropylcellulose, hydroxypropylmethylcellulose, cellulose nitrate, poly(vinyl alcohol), poly(vinyl chloride), polystyrene, polyethylene, polypropylene, poly(ethylene-co-vinyl acetate), polyesters, e.g., poly(hydroxybutyric acid), poly(hydroxyvalerianic acid-co-hydroxybutyric acid), poly(lactic acid), poly(glycolic acid), poly(lactic acid-co-glycolic acid), poly(epsilon(-caprolactones), poly(epsilon(-caprolactone-co-DL-lactic acid), polyanhydrides, e.g., poly(maleic anhydride), polyamides, albumin, gelatin, chitosan, collagen, pol(hydroxyalkyl)-L-glutamines, poly(gamma(-ethyl-L-glutaminate-co-glutamic acid), poly(L-leucine-co-L-aspartic acid), poly(proline-co-glutamic acid), poly(orthoesters), e.g., poly(alkyl 2-cyanoacrylates), polylysin, alginate, alginic acid, polyurethanes, poly(methyl methacrylate), poly(methyl methacrylate-co-methacrylic acid), poly(methacrylate-co-hydroxypropyl methacrylate).

Preparation of Composite Membranes

In a typical method, dried nano- and/or microparticles were dispersed in a solution containing at least one polymer such as ethylcellulose, poly(lactic acid), poly(lactic acid-co-glycolic acid), poly(epsilon(-caprolactones), and poly(orthoesters). The mixture was then poured into a glass ring and allowed to dry forming a membrane. Melting method can also be used for preparation of the composite membranes. In this method, the dried nano- and/or microparticles were mixed with powders of at least one polymer such as poly(ethyline-co-vinyl acetate). The powders were then melted forming a membrane upon cooled.

Applications

The polymeric system can applied for stimuli-responsive release of vaccine, for treatment of inflammation, infection, diabetes, arthritis, impotency, and cancer, as well as for separation and/or purification of solutes of different sizes in one batch. Examples of stimuli-responsive conditions are changes in temperature, pH, ionic strength, multivalent ions, and other chemicals and as appropriate under the circumstances providing higher dose of therapeutic agents. It can also be applied as diagnostic and monitoring tools, e.g., biosensors. Because of its sitimuli-responsive pore size, it can protect proteins and peptides from enzymatic degradation by preventing the enzymes from entering. Therefore, it will be useful for protein and peptide drug delivery. The system exhibits strong response to biochemical ions such as calcium ions and hence may be used for delivery of therapeutic agents in response to the stimuli of a biochemical process. Because of the ease of fabrication, the polymeric system can be applied as coating of a solid, semi-solid, or even liquid dosage forms providing stimuli-sensitive drug release. The present invention can also be used for encapsulation of live cells.

The following non-limiting examples are illustrative of the present invention:

EXAMPLES

Example 1

Preparation and Characterization of P(NIPAm/MAA) Nanoparticles

Poly(N-isopropylacrylamide-co-methacrylic acid) (PNIPAm/MAA) nanoparticles were prepared by an aqueous dispersion polymerization process. N-isopropylacrylamide (NIPAm, Eastman Kodak) was recrystallized in toluene and hexane. Methacrylic acid (MAA, Aldrich) was distilled to remove the inhibitor. N,N'-methylenebisacrylamide (BIS) (99%) and potassium persulfate (KPS) were purchased from Aldrich and used as received. Sodium dodecyl sulfate (SDS) was obtained from Mallinckrodt and used as received. The two monomers were dissolved in distilled water to make a molar ratio NIPAm/MAA=1/0 to 1/9 and a total concentration of 135 mM. After the incorporation of 6.4 mol % of BIS, a small amount of SDS was then added to the reaction mixture to a concentration level of 0.4 mM. The reaction mixture was purged with nitrogen and maintained at 70° C. The polymerization was started with the addition of a small amount of concentrated KPS solution to give a total concentration of 2.1 mM. The polymerization was carried out under nitrogen blanket at 70° C. for 4 hours at 200 rpm.

Purification of the Nanoparticles

The nanoparticles were enclosed in a standard cellulose dialysis tubing with a molecular weight cutoff of 12,000 to 14,000. After the sealing both ends with enclosure, the dialysis tubing was immersed in distilled and deionized (DDI) water. The water was changed twice daily for about 3 days, or until the conductivity of the water outside the dialysis tubing was comparable to that of distilled water.

Characterization of the Volume Phase Transition of the Nanoparticles

A small sample of nanoparticles was transferred to a glass cell and then diluted to a proper concentration using an aqueous medium such as DDI water, KCl solutions, $CaCl_2$ solutions, and buffer solutions of various pH. The cell was then placed in a sample holder at a constant temperature which was controlled by a computer. The particle size was determined with a dynamic light scattering particle sizer (NICOMP Model 370). The measurement was run for at least 3 cycles for each sample and the intensity-weighted particle diameter at 15–60° C. was recorded.

Figure 1:
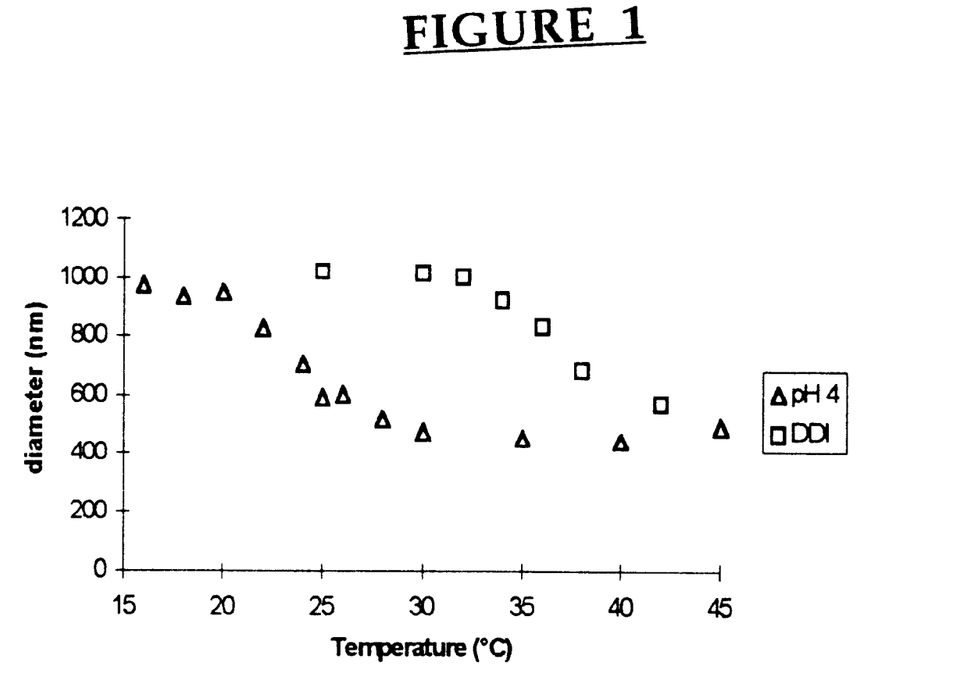
FIG. 1 is a graph showing the variation of particle diameter of PNIPAm/MAA nanoparticles with temperature in DDI water and pH 4 buffer.

FIG. 1 illustrates the particle diameter change with temperature in distilled deionized water and pH 4 buffer (0.5 M) for PNIPAm/MAA nanoparticles with NIPAm/MAA=1/0.1. A dramatic decrease in diameter is revealed for both cases indicating the volume phase transition. However, the transition temperature ($T_{tr}$) is shifted from ~37° C. in DDI water to ~23° C. in pH 4 buffer. The results suggest that the polymer particles are not only temperature sensitive but also pH responsive.

Preparation of Composite Membrane

In a typical preparation, 21.30 g of nanoparticles emulsion of PNIPAm/MAA were dried in an oven at ~55° C. 0.69 g of ethylcellulose (viscosity 100, Dow Chemical Company) was added to the dried nanoparticles, together with 24 g of absolute alcohol. The ethylcellulose clumps were broken down into smaller pieces using a spatula and the mixture was stirred and heated in a water bath at 70° C. overnight. The mixture was then taken out of the water bath and stirred inside a cold room at 4° C. for 2–3 days. The mixture was let to equilibrate at room temperature for about 1 day. The solution of ethylcellulose with dispersed PNIPAm/MAA nanoparticles were then cast in a glass ring which was covered with 6 pieces of paper towel and placed in a chamber. The relative humidity within the chamber was controlled by a drying agent, silicon gel, which was replaced by a fresh one whenever necessary. The composite membranes were then formed after ~2 days at room temperature within the chamber.

Characterization of the Membranes a) Determination of swelling, partition, and morphology of the membranes The swelling ratio of the membrane was obtained by measuring the weight of dry and wet membranes which had equilibrated with the media at various temperatures. Partition coefficient of the drugs between the membrane and the media was determined by the sorption method. Membrane samples were equilibrated with the drugs for more than two days until equilibrium and the decrease in the drug concentration was measured by UV spectroscopy. Cross-sectional morphology of the membrane was examined by scanning electron microscopy using A scanning electron microscope (Hitachi S-520) was used to determine the cross-sectional morphology of freeze-dried and fractured samples of the membranes.

Figure 2:
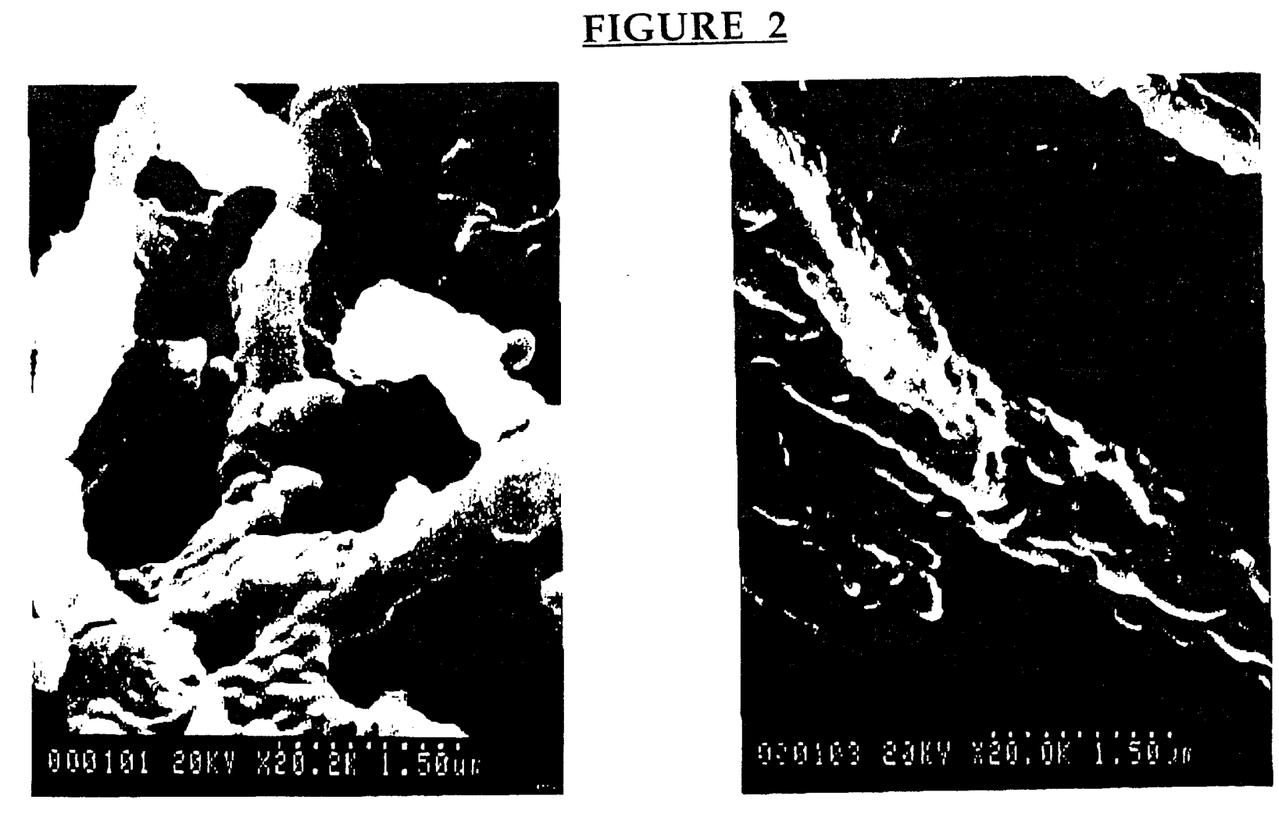
FIG. 2 shows SEM photographs of cross-section of the composite membrane (left) and the control (right) (ethylcellulose membrane).
Figure 3:
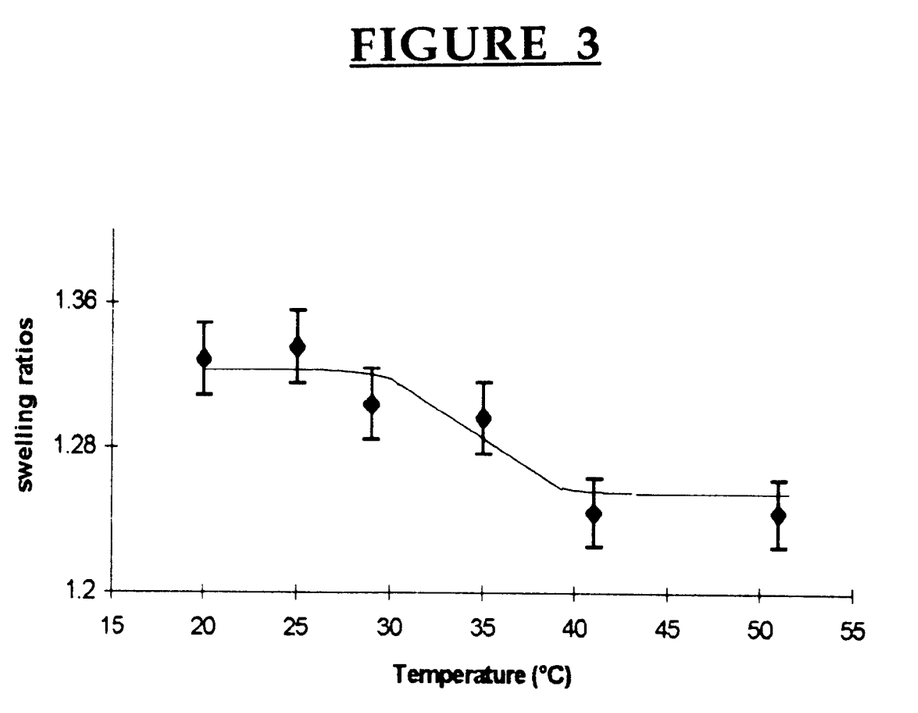
FIG. 3 is a graph showing the swelling ratio of the composite membrane changing with temperature in 0.0001 M KCl.

FIG. 2 compares the SEM photograph of cross-section of the composite membrane with that of a ethylcellulose membrane. A more porous structure and presence of the nanoparticles were revealed. The pores, originally occupied by the swollen particles, formed as the particles collapsed when they were dried prior to the measurement. Similarly, the pores were also formed at a higher temperature or lower pH when the particles deswelled. FIG. 3 shows that the swelling ratio of the composite membrane is a function of temperature and exhibits a transition at ~35° C.

b) Measurement of contact angle

Figure 4:
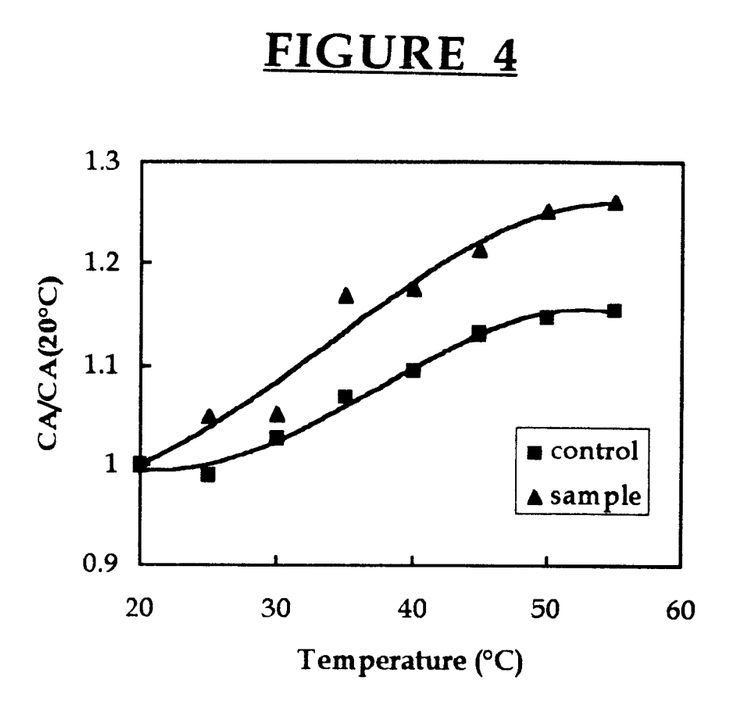
FIG. 4 is a graph showing the effect of temperature on the relative contact angle of DDI water on the composite membrane and the control.

The contact angle (CA) of water on the membranes was measured using a goniometer (Model 100-00 Rame-Hart Inc.). The temperature in the sample chamber was controlled by a water bath (Haake D8). The samples were equilibrated for 5 minutes at various temperatures prior to the measurements. FIG. 4 shows that the increase in contact angle of distilled water on the composite membrane with temperature is more significant than that of control (ethylcellulose membrane). This implies the temperature-dependent surface hydrophobicity of the composite membrane.

Characterization of Stimuli-responsive Permeation of the Membranes

Permeation of solutes of various molecular sizes through the membrane was determined using a side-by-side diffusion cell. The solution in the receptor cell was pumped to a UV cell with a peristaltic pump. The amount of solute permeated was assayed by a diode array spectrophotometer (HP 8452A). The pH of the medium was adjusted either by addition of sodium hydroxide and hydrochloric acid.

Macromolecules, e.g., chymotrypsin (MW 22,000), could not penetrate through the membrane at the studied temperatures.

b) pH-responsive permeation

Figure 8:
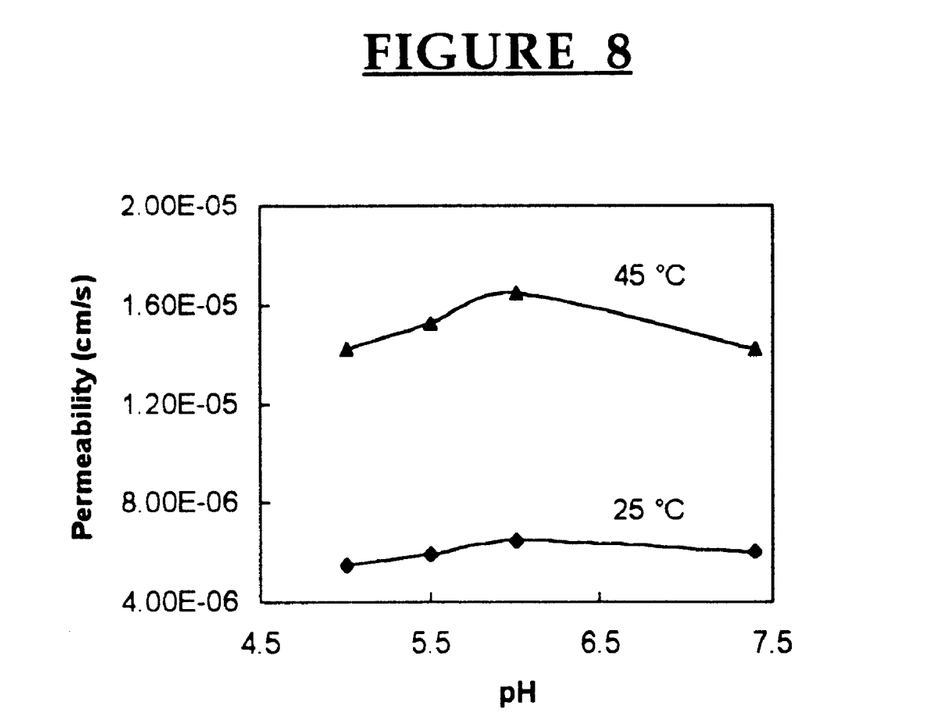
FIG. 8 is a graph showing the effects of pH on the permeation of theophylline at 20 and 45° C.
Figure 8A:
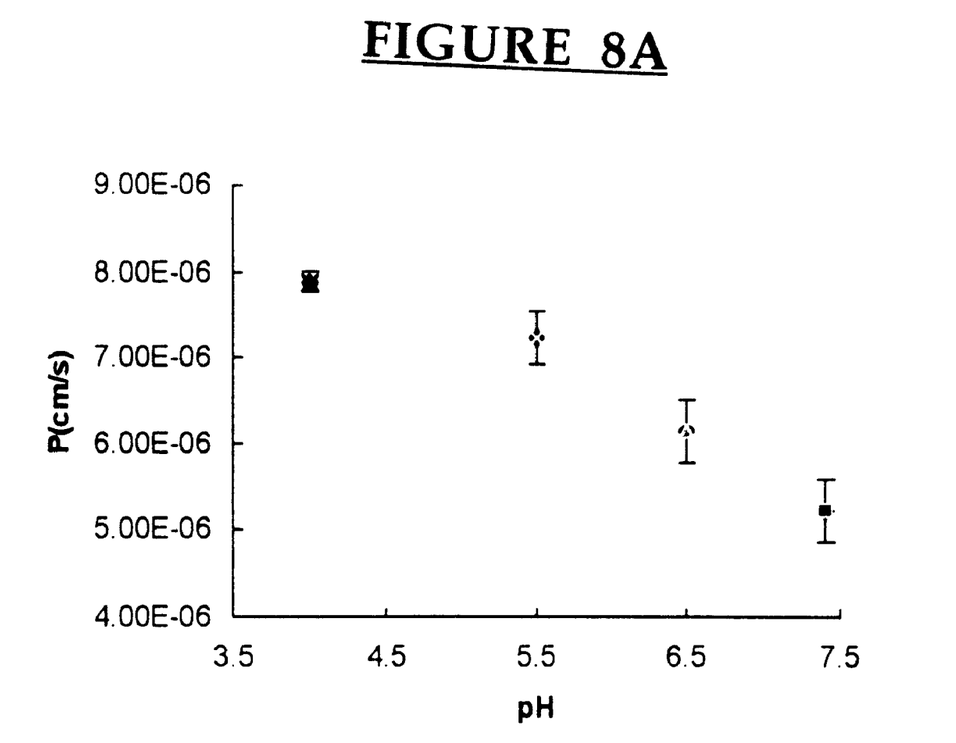
FIG. 8A is a graph showing the effects of pH on the permeation of vitamin B12.

The permeability of theophylline at various pH and two different temperatures is illustrated in FIG. 8. A peak permeability at ~ pH 6.25 is revealed at both temperatures, especially at 45° C. This implies that an increased permeation may be expected at a site of inflammation with a combination of hyperthermia and lower pH.

c) Dependence of permeation on ionic strength and divalent ions

Figure 9:
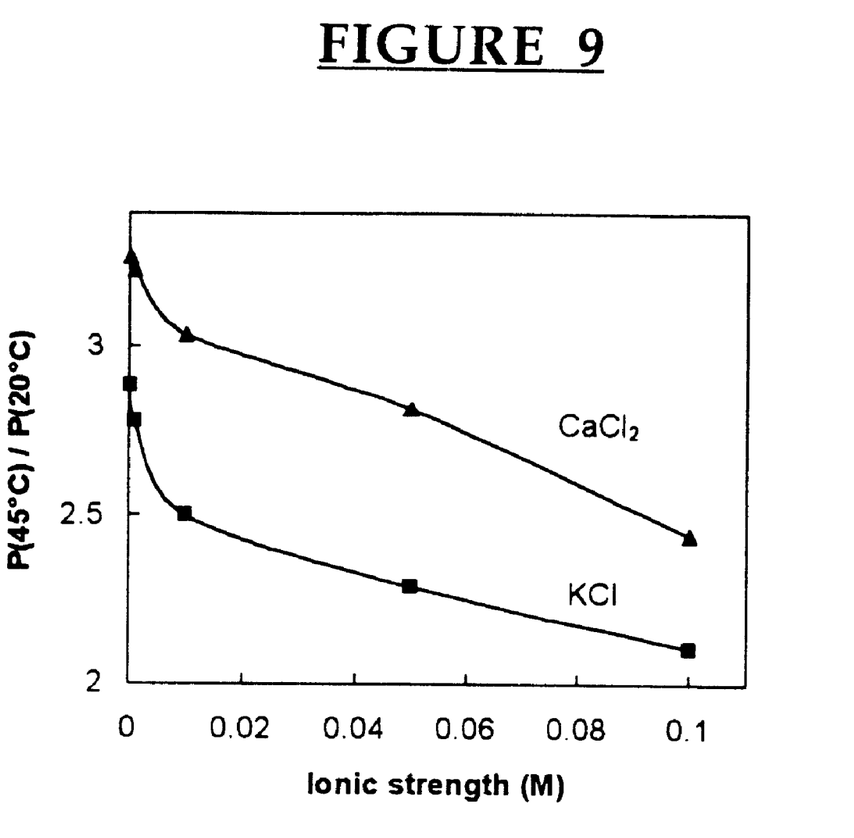
FIG. 9 is a graph showing the effect of the monovalent and divalent ions on the degree of enhancement of permeability of theophylline across the composite membrane.

FIG. 9 depicts that the permeability increment of theophylline as temperature is increased from 20° C. to 45° C. is reduced with increasing ionic strength. However, in the presence divalent ions, $Ca^+$, the permeability increment is always higher than that with monovalent ions, $K^+$. This observation suggests that the permeation is responsive to the divalent ions.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Preparation method | Ability to control pore size | No reaction required | Transition temperature close to physiological temperature | No purification required | No leakage of responsive component | Mechanical strength | Positive response to temperature |
|---|---|---|---|---|---|---|---|
| grafting polymerization | X | X | X | X | ✓ | strong | ✓ |
| vacuum filtration | X | ✓ | X | ✓ | X | strong | ✓ |
| hydrogel synthesis by polymerization | ✓ | X | X | X | ✓ | weak | X |
| This invention | ✓ | ✓ | ✓ | ✓ | ✓ | strong | ✓ |

X - means "NO"
✓ - means "YES"

a) Temperature-responsive permeation

Figure 5:
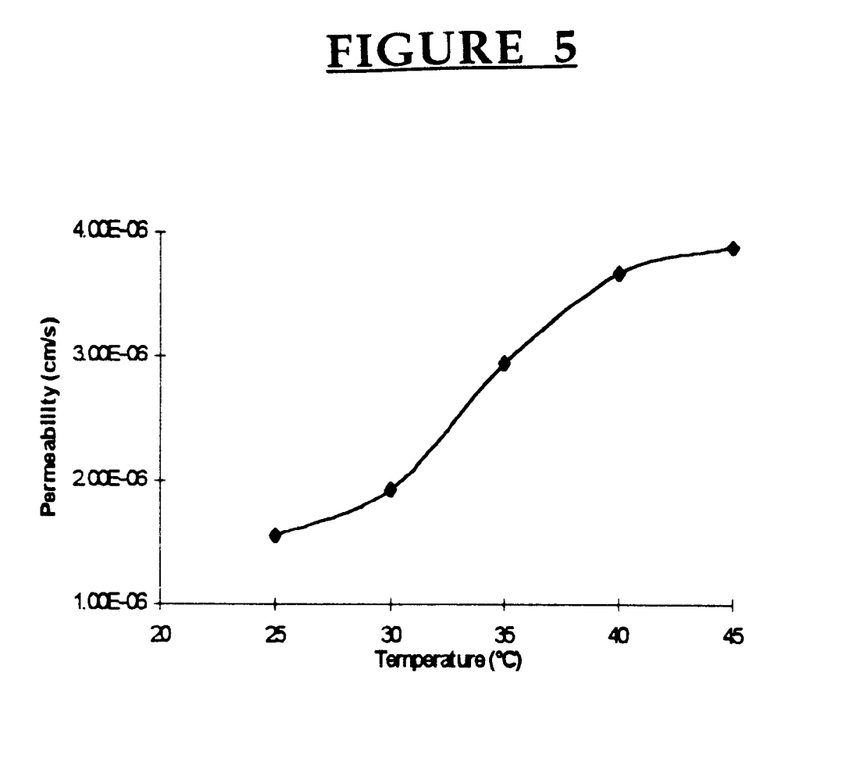
FIG. 5 is a graph showing the variation of permeability of acetaminophen across the composite membrane with temperature in DDI water.
Figure 6:
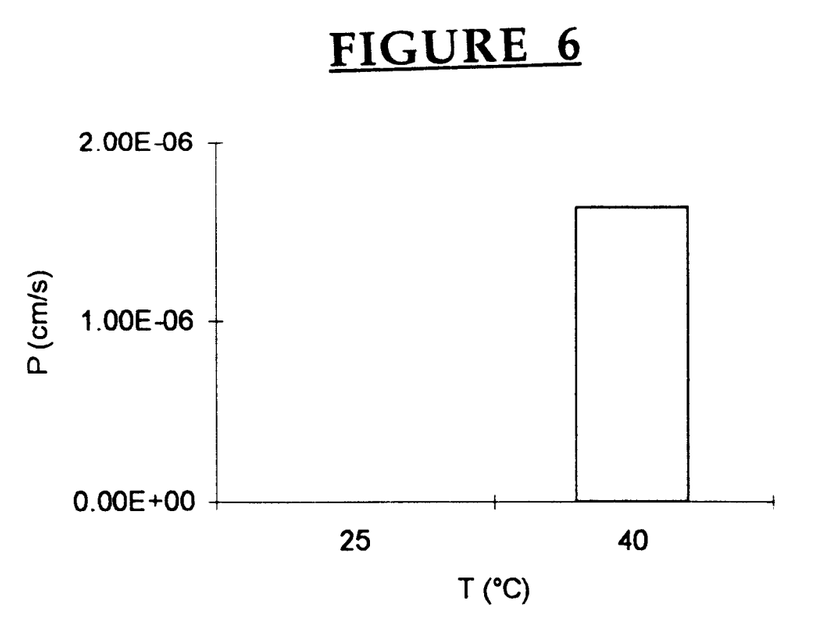
FIG. 6 is a graph showing the permeability of vitamin B12 at 25 and 40° C.
Figure 7:
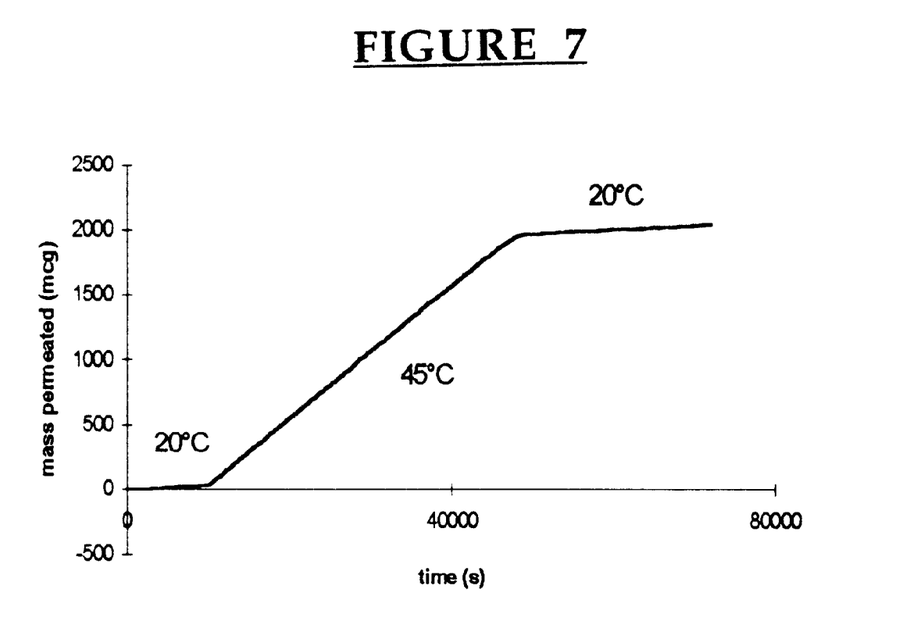
FIG. 7 is a graph showing permeation profile of vitamin B12 across the composite membrane in $3.33 \times 10^{-2}$ mM $CaCl_2$.

FIG. 5 illustrates that permeability of acetaminophen across the composite membrane increases continuously with increasing temperature and experiences a drastic increase as temperature is raised from 30 to 40° C. This suggests a transition of permeability at ~35° C. which is similar to the transition of the swelling ratio. The ratio of the permeability at 40° C. to that at 25° C. is about 2.6 times. Like acetaminophen, permeability of theophylline increased about 2.8 times. More significant change in permeability was observed for larger solutes such as vitamin B12. FIG. 6 depicts that almost negligible permeation of $V_{B12}$ across the membrane into water at 25° C. compared with that at 40° C. In the presence of a bivalent salt, $CaCl_2$, the permeation of $V_{B12}$ was measurable. However, as shown in FIG. 7, its permeability at 45° C. was much higher, about 11-fold of that at 20° C. as calculated from the slopes of the curves.

TABLE 2

| Permeants | Molecular weight | P(45° C.)/P(20° C.) in 0.0001M KCl |
|---|---|---|
| Acetaminophen | 151.16 | 2.20 |
| Theophylline | 180.17 | 2.88 |
| Vitamin $B_{12}$ | 1355.42 | 11.0 |
| Chymotrypsin | ~20,000 | No permeation at both temperatures |

Full Citations For References Referred To In The Specification

1. Sherwood L. *Human Physiology from cells to systems.* Wadsworth Publishing Company, California. 1997 p. 121, 165.

2. Robbins S L, Kumar V, Cotran R S (eds). *Robbins Pathologic Basis of Disease*. W. B. Saunders Company, Pennsylvania. 1994. p. 51–92.
3. Punnia-Moorthy A. Evaluation of pH changes in inflammation of the subcutaneous air pouch lining in the rat, induced by carrageenan, dextran and Staphylococcus aureus. *J. Oral Pathol.* 16 (1987) 36–44.
4. Martin G R, Jain R K. Noninvasive measurement of interstitial pH proifiles in normal and neoplastic tissue using fluorescence ratio imaging microscopy. *Cancer Research* 54 (1994) 5670–74.
5. Field S B, Hand J W eds. *An Introduction to the Practical Aspects of Clinical Hyperthermia*. London, England: Taylor and Francis, 1990.
6. Chung D J , Ito Y, Imanishi Y. An insulin-releasing membrane system on the basis of oxidation reaction of glucose. *J. Controlled Release* 18 (1992) 45–54
7. Kim S W, Okano T, Bae Y H et al. Thermally on-off switching polymers for drug permeation and release. *J. Controlled Release* 11(1990) 255–265.
8. Iwata H, Oodate M, Uyama Y et al. Preparation of temperature-sensitive membranes by graft polymerization onto a porous membrane. *Journal of Membrane Science* 55 (1991) 119–130.
9. Lee Y M, Shim J K. Preparation of pH/temperature responsive polymer membrane by plasma polymerization and its riboflavin permeation. *Polymer* 38 (1997) 1227–32
10. Spohr R, Reber N, Wolf A et al. Thermal control of drug release by a responsive ion track membrane observed by radio tracer flow dialysis. *Journal of Controlled Release* 50 (1998) 1–11.
11. Chun S W, Kim J D. A novel hydrogel-dispersed composite membrane of poly(N-isopropylacrylamide) in a gelatin matrix and its thermally actuated permeation of 4-acetamidophen. *Journal of Controlled Release* 38 (1996) 39–47.
12. Park Y S, Ito Y, Imanishi Y. Permeation control through porous membranes immobilized with thermosensitive polymer. *Langmuir* 14 (1998) 910–914.
13. Lin Y Y, Chen K S, Lin S Y. Development and investigation of a thermo-responsive cholesteryl oleyl carbonate-embedded membrane. *Jounal of Controlled Release* 41 (1996) 163–170
14. Okano T, Sakurai Y, Yoshida R et al. Positive thermosensitive pulsatile drug release using negative thermosensitive hydrogels. *Journal of Controlled Release.* 32 (1994) 97–102.
15. Lemmer B ed. *From the biological clock to chronopharmacology*. Stuttgart, Germany, medpharm, 1996
16. Matson S L. 'Membrane bioseparation' in: *Membrane separation technology principles and applications*, R D Noble, S A Stern (ed.), Elsevier, Amsterdam, 1995, pp. 353–413
17. Wu X Y, Lee P I. Preparation and characterization of thermal and pH sensitive nanospheres. *Pharm. Res.* 10 (1993) 1544–47.
18. Wu X, Pelton R H, Hamielec A E et al. The kinetics of poly(N-isopropylacrylamide) microgel latex formation. *Colloid Polym Sci.* 272 (1994) 467–77.

We claim:

1. A composition for a composite polymer system comprising particles of a stimuli-responsive polymer dispersed within a matrix, said matrix comprising at least one second polymer, wherein said at least one second polymer is non-swellable, hydrophobic and membrane-formable.

2. A composition according to claim 1 wherein the stimuli-responsive polymer is selected from the group consisting of polymers of R-acrylamide, R1-acrylate and R2-acrylic acid; and polyethylene glycol, where R, R1, and R2 may each be H or alkyl.

3. A composition according to claim 2 wherein said second polymer is selected from the group consisting of polysaccharides; cellulose; polyesters; polyanhydrides; poly (othoesters); and polyurethane.

4. A composition according to claim 3 wherein the composition is biocompatable and biodegradable.

5. The composition according to claim 1 comprising poly(N-isopropylacrylamide-co-methacrylic acid) and ethylcellulose.

6. A composite polymer system according to claim 1 wherein the stimuli-responsive polymer is swellable.

7. A composition according to claim 1 wherein said second polymer is also, membrane forming.

8. A composition according to claim 7 wherein the second polymer also forms a continuous phase with said stimuli-responsive polymer.

9. A composition according to claim 1 wherein said second polymer is selected from the group consisting of cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly (hydroxybutyric acid), poly(hydroxyvalerianic acid-co-hydroxybutyric acid), poly(lactic acid), poly(glycolic acid), poly(lactic acid-co-glycolic acid), poly(epsilon (-caprolactones), poly(epsilon(-caprolactone-co-DL-lactic acid), poly(maleic anhydride), polyamides, gelatin, chitosan, collagen, poly(hydroxyalkyl)-L-glutamines, poly (gamma(-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate).

10. The composition according to claim 1, wherein the stimuli-responsive polymer particles form channels in the matrix in response to changes in external stimuli.

11. A method of preparing a composite polymer system according to claim 1 comprising: (a) preparing particles with a stimuli-responsive polymer; (b) adding and mixing at least one second polymer under conditions which permit dispersion of the particles in the second polymer; and (c) casting the resulting composite polymer system, wherein said at least one second polymer is non-swellable and hydrophobic.

12. A method according to claim 11 wherein the step of mixing is carried out by a method selected from the group consisting of melting the polymers and mixing the polymers in solution.

13. A method according to claim 11 wherein the stimuli-responsive polymer is swellable.

14. A method of solute separation and filtration comprising the following steps:
   (i) preparing a composite polymer system according to the method of claim 11;
   (ii) incorporating a substance within the system; and
   (iii) applying the system under conditions which result in solute separation and filtration.

15. A method of temperature, pH and ionic strength, biochemical or ion-responsive drug delivery comprising the following steps:
   (i) preparing a composite polymer system according to the method of claim 11;
   (ii) incorporating a substance within the system; and (iii) applying the system under conditions which result in temperature, pH and ionic strength, biochemical or ion-responsive drug delivery.

16. A method for diagnosis and monitoring comprising the following steps:
   (i) preparing a composite polymer system according to the method of claim 11;
   (ii) incorporating a substance within the system; and
   (iii) applying the system under conditions which result in diagnosis and monitoring.

17. A method of protein and peptide drug delivery comprising the following steps:
   (i) preparing a composite polymer system according to the method of claim 11;
   (ii) incorporating a substance within the system; and
   (iii) applying the system under conditions which result in protein or peptide drug delivery.

18. A method of coating and microencapsulation of solid dosage forms or live cells comprising the following steps:
   (i) preparing a composite polymer system according to the method of claim 11;
   (ii) incorporating a substance within the system; and
   (iii) applying the system under conditions which result in coating and microencapsulation of solid dosage forms or live cells.

19. A method according to claim 11 wherein said second polymer is also, membrane forming.

20. A method according to claim 19 wherein the second polymer also forms a continuous phase with said stimuli-responsive polymer.

21. A method according to claim 11 wherein the stimuli-responsive polymer is selected from the group consisting of polymers of R-acrylamide, R1-acrylate and R2-acrylic acid; and polyethylene glycol, where R, R1, and R2 may each be H or alkyl.

22. A method according to claim 21 wherein said second polymer is selected from the group consisting of polysaccharides; cellulose; polyesters; polyanhydrides; poly (othoesters); and polyurethane.

23. A method according to claim 21, wherein said second polymer is selected from the group consisting of cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly (hydroxybutyric acid), poly(hydroxyvalerianic acid-co-hydroxybutyric acid), poly(lactic acid), poly(glycolic acid), poly(lactic acid-co-glycolic acid), poly(epsilon(-caprolactones), poly(epsilon(-caprolactone-co-DL-lactic acid), poly(maleic anhydride), polyamides, gelatin, chitosan, collagen, poly(hydroxyalkyl)-L-glutamines, poly (gamma(-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate).

* * * * *